United States Patent [19]
Desai

[11] Patent Number: 6,052,612
[45] Date of Patent: *Apr. 18, 2000

[54] CATHETER FOR MEDIA INJECTION

[76] Inventor: Jawahar M. Desai, 8755 Petite Creek Way, Roseville, Calif. 95661

[*] Notice: This patent is subject to a terminal disclaimer.

[21] Appl. No.: 09/049,841

[22] Filed: Mar. 27, 1998

Related U.S. Application Data

[63] Continuation of application No. 08/476,122, Jun. 7, 1995, Pat. No. 5,857,464.

[51] Int. Cl.⁷ ..................................................... A61B 6/00
[52] U.S. Cl. .......................... 600/435; 604/105; 604/246; 604/247
[58] Field of Search .................................... 604/104–105, 604/247, 246, 530–532; 600/435

[56] References Cited

U.S. PATENT DOCUMENTS

| | | |
|---|---|---|
| 985,865 | 3/1911 | Turner . |
| 1,719,428 | 7/1929 | Friedman . |
| 2,649,092 | 8/1953 | Wallace . |
| 3,331,371 | 7/1967 | Rocchi et al. . |
| 3,568,659 | 3/1971 | Karnegis . |
| 3,670,732 | 6/1972 | Robinson . |
| 3,734,083 | 5/1973 | Kolin . |
| 3,757,773 | 9/1973 | Kolin . |
| 3,799,172 | 3/1974 | Szpur . |
| 3,884,220 | 5/1975 | Hartnett . |
| 4,019,515 | 4/1977 | Kornblum et al. . |
| 4,023,559 | 5/1977 | Gaskell . |
| 4,029,104 | 6/1977 | Kerber . |
| 4,137,906 | 2/1979 | Akiyama et al. . |
| 4,154,242 | 5/1979 | Termanini . |
| 4,327,722 | 5/1982 | Groshong et al. . |
| 4,531,943 | 7/1985 | Van Tassel et al. . |
| 4,669,463 | 6/1987 | McConnell . |
| 4,699,611 | 10/1987 | Bowden . |
| 4,734,094 | 3/1988 | Jacob et al. . |
| 4,781,682 | 11/1988 | Patel . |
| 4,800,890 | 1/1989 | Cramer . |
| 4,813,934 | 3/1989 | Engelson et al. . |
| 4,865,017 | 9/1989 | Shinozuka . |
| 4,871,356 | 10/1989 | Haindl et al. . |

(List continued on next page.)

OTHER PUBLICATIONS

Abbott, Lipton, Hayashi and Lee; "A Quantitative Method for Determining Angiographic Jet Energy Forces and Their Dissipation: Theoretic and Practical Implications"; *Catheterization and Cardiovascular Diagnosis*; 1977; vol. 3; pp. 139–154.

Abbott, Lipton, Kosek, Hayashi and Lee; "Cardiac Trauma from Angiographic Injections"; *Circulation*; Jan. 1978; vol. 57; No. 1; pp. 91–98.

Hildner, Furst, Krieger, Chengot, Javier, Tolentino and Samet; "New Principles for Optimum Left Ventriculography"; *Catheterization and Cardiovascular Diagnosis*; 1986; vol. 12; pp. 266–273.

Lubell; "Angiography", *Cath–Lab Digest*, Jul./Aug. 1994, No. 7, pp. 15–16, 18, 20–21.

*Primary Examiner*—Mark Bockelman
*Attorney, Agent, or Firm*—Majestic, Parsons, Siebert & Hsue

[57] ABSTRACT

An improved endocardial catheter includes a plurality of longitudinally extending openings adjacent intermediate portions at its distal end. The catheter is actuable from a retracted or collapsed mode, wherein the sealed openings are arranged around the tubular catheter surface, to an expanded mode. The plurality of longitudinal openings in the catheter wall enable radial expansion of the tubular surface at the distal end so that intermediate portions of the tubular catheter surface are moved to an operative position radially outward from their position in the retracted mode. In the expanded position, the intermediate portions form wings around the distal end, revealing a cavity within the tubular catheter for the release of contrast material or other fluid into endocardial sites through the longitudinal openings.

16 Claims, 9 Drawing Sheets

U.S. PATENT DOCUMENTS

| | | |
|---|---|---|
| 4,911,163 | 3/1990 | Fina . |
| 4,940,064 | 7/1990 | Desai . |
| 5,030,210 | 7/1991 | Alchas . |
| 5,035,705 | 7/1991 | Burns . |
| 5,078,681 | 1/1992 | Kawashima . |
| 5,085,635 | 2/1992 | Cragg . |
| 5,104,389 | 4/1992 | Deem et al. . |
| 5,188,602 | 2/1993 | Nichols . |
| 5,193,533 | 3/1993 | Body et al. . |
| 5,350,363 | 9/1994 | Goode et al. . |
| 5,381,790 | 1/1995 | Kanesaka . |
| 5,409,463 | 4/1995 | Thomas et al. . |
| 5,443,449 | 8/1995 | Buelna . |
| 5,613,950 | 3/1997 | Yoon . |
| 5,702,365 | 12/1997 | King . |

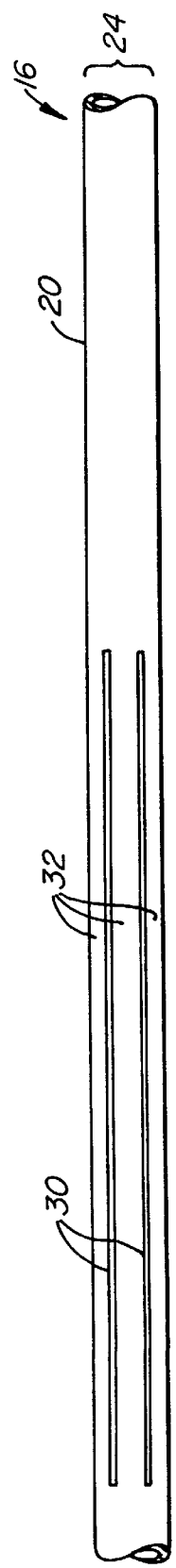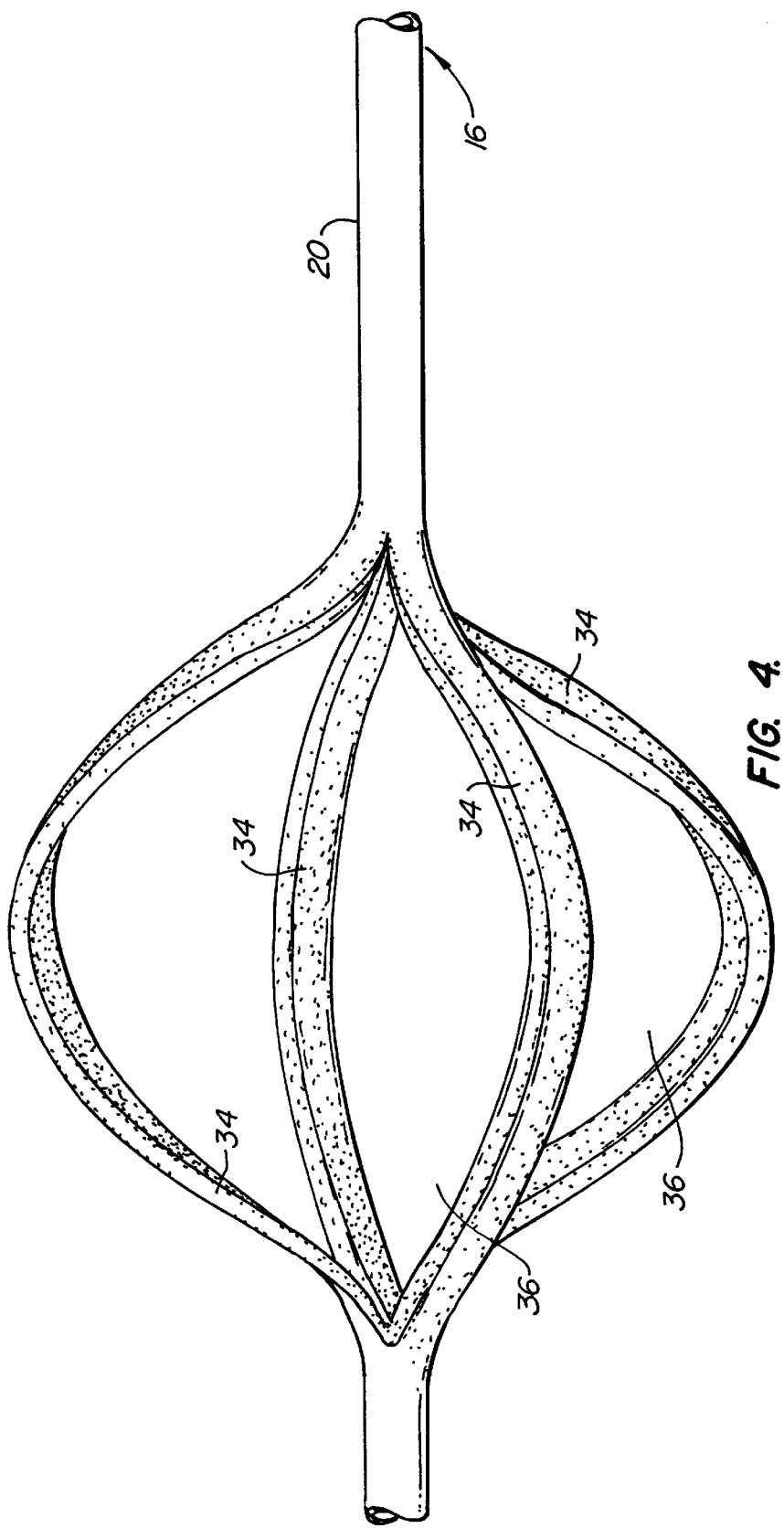
FIG. 3.
FIG. 4.

CATHETER FOR MEDIA INJECTION

This is a continuation of U.S. application Ser. No. 08/476,122 filed Jun. 7, 1995, now U.S. Pat. No. 5,857,464.

BACKGROUND OF THE INVENTION

This invention relates to medical devices, and in particular to angiographic catheters. Angiographic catheters are long, narrow, thin-walled tubes that are percutaneously inserted into the human or animal vascular system for therapeutic or diagnostic purposes. Most diagnostic catheters have a series of side-holes in varied configurations near the distal end, as well as an open end-hole at the distal end tip. The end-hole allows the catheter to be passed over and guided by a wire which has been inserted into the vascular system through a hollow cannula placed in a blood vessel, after which the guide wire is withdrawn. The smaller side-holes and end-hole allows injection of radiopaque contrast material into the blood stream surrounding the distal end, so as to produce an image of the outline of a chamber or a blood vessel (an angiogram) on X-ray film or other graphic medium. During the diagnostic angiography process, the contrast material is normally injected at a rapid rate using a power injector. The contrast material is forcefully discharged from the end-hole and side-holes at the distal end of the catheter.

Problems with forceful discharge of contrast material through the end-hole and smaller side-holes of an angiographic catheter are manifest. Forceful discharge can create a jet effect. The end-hole jet effect produces undesirable recoil of the catheter, thereby shifting the catheter from a desired position within a chamber or a vessel, e.g. aortic root. Catheter jets can also produce a dangerous complication, subintimal injection of the contrast material, in which the jets tunnel into the wall of the blood vessel, sometimes resulting in acute occlusion of the vessel and in a chamber like left ventricle can cause subintimal injection resulting in significant damage to endothelium. When dye is injected in a chamber like left ventricle, an end-hole or side-hole jet can also cause premature ventricular contractions (PVCs), ventricular tachycardias (groups of three or more PVCs) and other arrhythmias which endanger the patient, lengthen the time of exposure to X-rays required for satisfactory opacification, and often result in unintelligible chamber opacification in an angiogram made during their occurrence.

A further complication resulting from pressurized discharge of contrast material through the end and side-holes of known catheters is the need for more contrast material than is optimally desired to produce the angiogram. Available angiographic catheters require as much as 50 to 55 milliliters (ml) of contrast material to satisfactorily outline a human ventricle. Currently available contrast material can cause undesirable generalized allergic reactions like anaphylaxis and renal failure. Also, the amount of material used dictates the time required to inject the material and, therefore, affects both the required length of exposure to dangerous X-rays as well as the probability of obtaining a satisfactory angiogram. There is, therefore, a need in the field to reduce the amount of contrast material used in cardiac angiography.

Most catheters presently used for rapid flush angiography are configured with a circular loop or "pigtail" at the distal end. These pigtail-type catheters are provided with a plurality of side-holes through which only approximately 40% of the contrast medium is discharged at the desired position within the chamber. Although the looped end of the catheter decreases somewhat the chance of subintimal injection, the open end-hole still allows approximately 40% of the contrast material to exit the end-hole. The material exiting the end-hole creates a strong jet of material placed away from the optimal position for vessel or chamber opacification. To overcome the limitations of the pigtail catheter in cardiac angiography, various modifications have been attempted to the pigtail configuration, such as a bend at an acute angle in the distal portion of the catheter and adding multiple holes on the shaft, both to decrease the jet effect. However, these modifications have not satisfactorily alleviated the problems associated with the use of any catheter which has an open end-hole.

The smaller side-holes located adjacent the distal end of known angiographic catheters are flawed as well. Such side-holes allow a very limited volume of material to form the bolus needed for opacification of the chamber, thereby elongating the time needed to adequately outline the chamber in the angiogram. Longer X-ray exposure endangers the patient and decreases the likelihood of obtaining satisfactory angiogram results. Moreover, side-holes can cause pressure jets leading to PVCs and other arrhythmias, as outlined above.

Although adding additional side-holes may increase the volume of material allowed into the vessel while dissipating pressure jets, such an increase may result in a distal region of less strength than the main body of the catheter tube. As a result of this reduced strength, complaints have arisen as to some currently-available angiographic catheters from physicians, who have reported that in clinical use, as they have attempted to put the pigtail tip through the aortic valve, the distal tip area in which the side-holes reside sometimes buckles.

It is therefore desirable to increase the volume of the bolus of contrast material allowed to flow out of an angiographic catheter in a short time span without decreasing the catheter's rigidity near the distal end, and without inducing PVCs, ventricular tachycardias or other arrhythmias. It is also desirable to decrease the amount of material needed to create the bolus of material within the opacified vessel.

SUMMARY OF THE INVENTION

This invention is directed to an endocardial catheter. The catheter preferably incorporates an end-hole valve means and deformable wings near the distal end. The end-hole valve means functions to curtail undesirable jet effects and to decrease the amount of contrast material and radiation required for optimal angiographic results. The deformable wings adjacent the distal end function to facilitate low-pressure entry of contrast material at a high rate of flow to optimize chamber opacification and increase the patient's safety and comfort.

Thus, one object of the present invention is to provide a catheter in the form of a hollow, thin-walled tube having a plurality of circumferentially-spaced longitudinally extending slits through the thin wall adjacent the distal end. These slits form a plurality of circumferentially-spaced longitudinally extending flexible intermediate portions of the thin wall adjacent the slits. The flexible intermediate portions are capable of forming a plurality of wings extending from the tube to provide for the discharge of fluid from the passageway out through the open slits of the tube near the distal end.

A further object of the present invention is to provide a flexible intermediate portion, shaped during fabrication to retain a winged shape at the distal end. An external, removable cannula dimensioned to sealingly fit over and collapse the tube to its maximum length and minimum width and to compress the wings until they return to a position flush with the wall of the tube can be incorporated.

Still another object of the present invention is to provide a catheter including and insertable over a guidewire or other device to facilitate entry of the catheter's distal end into a blood vessel. The catheter may also include a valve sealingly fit into the distal end of the main passageway, wherein the valve opens during the passage of the guidewire through the tube and valve. The catheter may otherwise include a valve for at least partially closing the main passageway at the distal end of the tube, wherein the valve comprises a plurality of resilient flaps which flex when exposed to the force of fluid pressure originating within the passageway.

The apparatus of the present invention, including an end-hole valve means as well as a plurality of circumferentially-spaced intermediate portions capable of forming wings, increases the likelihood of satisfactory vessel or chamber opacification, decreases the number of cardiac arrhythmias and endocardial damage resulting from pressure jet effects, and decreases the amount of contrast material and radiation required for optimal chamber or vessel opacification when used in cardiac angiography, without significantly reducing the catheter's resistance to buckling when used in highly tortuous endocardial procedures.

Still other objects and advantages of the present invention will become apparent to those skilled in the art as the disclosure is made in the following description of the best mode contemplated by me of carrying out my invention. As will be realized, the invention is capable of other embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

The above and other features and aspects of the present invention will become more apparent upon reading the following detailed description in conjunction with the accompanying drawings, in which:

FIG. 3 is a fragmentary perspective view of the preferred catheter according to the present invention with the intermediate portions in the initial, non-extended position;

FIG. 4 is a view similar to FIG. 3, but with the intermediate portions in the outwardly extended position forming wings;

FIG. 5-A is a longitudinal cross-sectional view of an alternate embodiment of the preferred catheter with the intermediate portions in the initial, non-extended position.

FIG. 13-B is a photo of a left ventricular angiogram with a pigtail catheter;

FIG. 14-B is a bargraph showing a comparison between the new and pigtail catheters illustrating differences in dye density;

FIG. 14-C is a bargraph showing a comparison between the new and pigtail catheters further illustrating differences in dye density;

FIG. 16-B is a photo of dye being injected into the left ventricle through a pigtail catheter;

DETAILED DESCRIPTION OF THE PREFERRED EMBODIMENT

Figure 1:
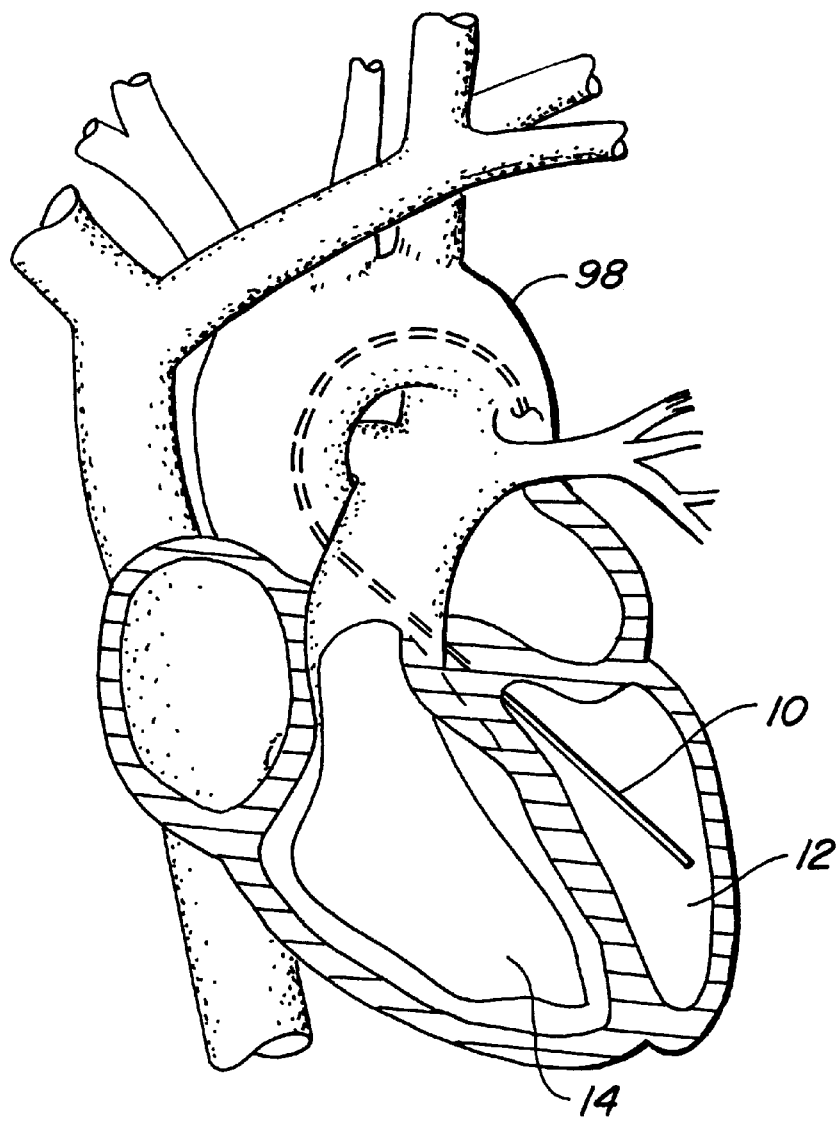
FIG. 1 is a front elevational view of a human heart in partial cross-section illustrating the distal end of the inventive catheter within an endocardial vessel, namely, the left ventricle.

The catheter 10 of the instant invention, shown in FIG. 1, is placed within a heart ventricle 12. As shown, the catheter is placed within the left ventricle, although it could as easily be placed within the right ventricle 14 or any other endocardial chamber or site.

Figure 2:
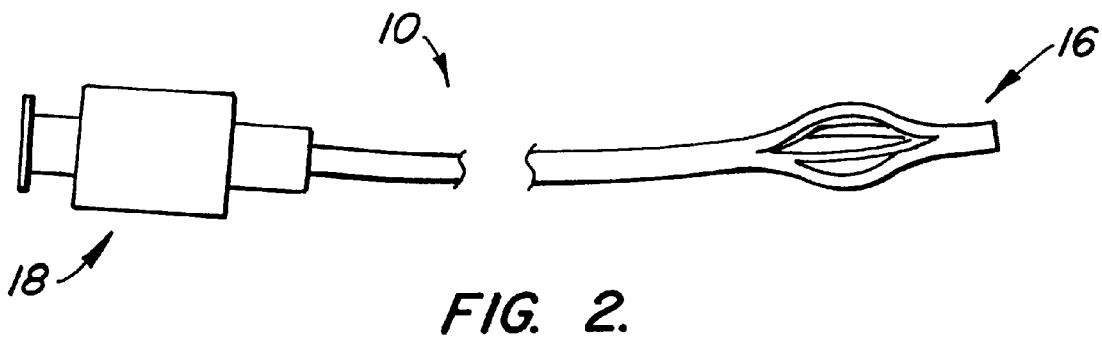
FIG. 2 is a front elevational view of the preferred catheter.

Turning to FIG. 2, there is shown the inventive catheter 10 having a distal end 16 and a proximal end 18 at the opposite end thereof. A standard fitting 19 enables connecting the catheter to a source of fluid under pressure, such as a power injector (not shown).

As shown in FIGS. 3 and 4, the distal end 16 of the catheter is comprised of a generally hollow flexible tube portion 20 of an outer diameter 24 small enough to be passed through the blood vessels and into the heart. Tube 20 may be made of flexible material such as plastic or Dacron brand material, but is preferably made of material with a "set" or "memory" for reasons noted below. As shown in these figures and in FIGS. 5 and 6, tube 20 has an inner bore 22, of a lesser diameter than the outer diameter 24, forming a passageway 50 through which a guidewire 26 or radiopaque contrast material (not shown) may pass. The distal end 16 may be either normally straight as shown in the drawings, or may be shaped into a circular pigtail configuration similar to that of presently used angiographic catheters. The principles of the invention therefore can be applied to pigtail catheters which are used extensively in ventriculography.

Referring again to FIG. 3, the area adjacent distal end 16 is in its fully retracted position. Circumferentially-spaced slits 30 partially extend along the length of tube 20 near the distal end and sealingly close when tube 20 is at its maximum length and minimum diameter. Defined between slits 30 are intermediate portions 32. To ensure tube 20 remains in its fully extended position shown in FIG. 3 during placement of catheter 10, removable sheath 28, shown in this figure and in FIG. 5, may be sealingly fit around tube 20, forcing the tube to its maximum length and minimum diameter shown.

Figure 7:
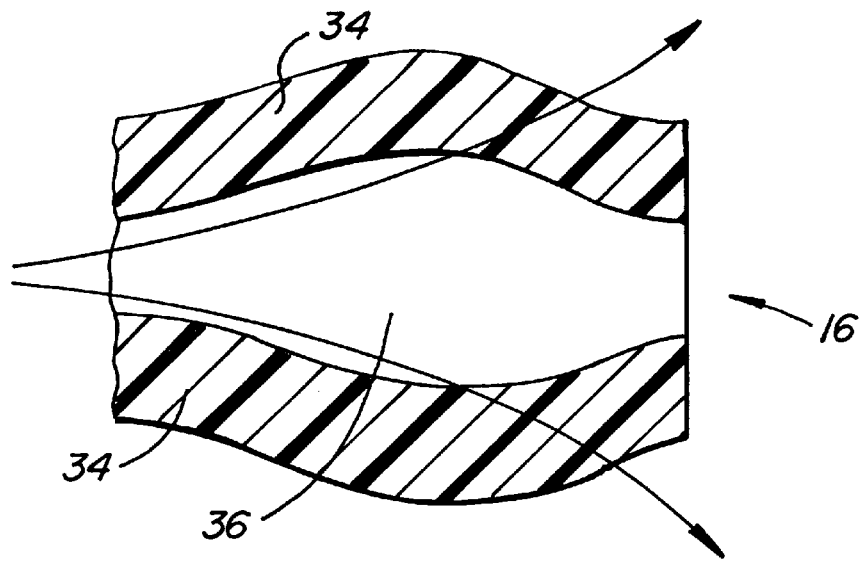
FIG. 7 is a longitudinal cross-sectional view of the preferred catheter with the intermediate portions in the outwardly extended position forming wings.
Figure 8:
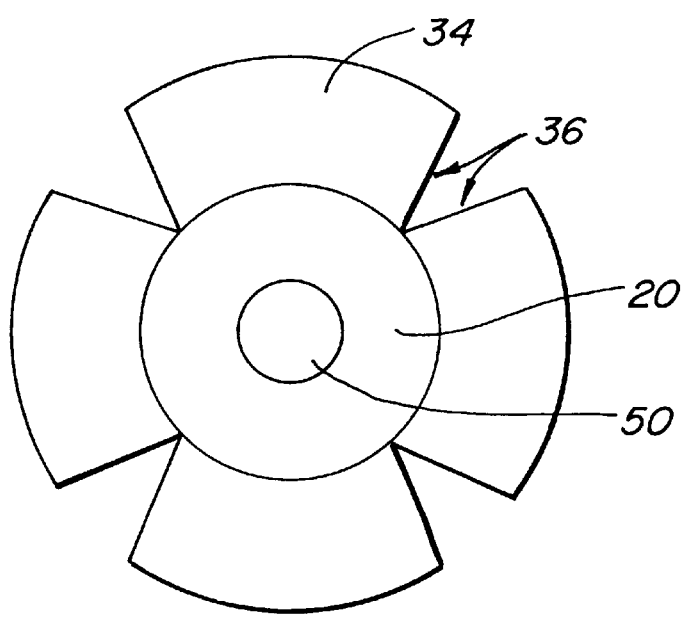
FIG. 8 is a right end elevational view of the same.

In FIGS. 4, 7 and 8, the area adjacent distal end 16 is in its fully expanded position, which is caused by the "memory" of the plastic from which it is made. Intermediate portions 32 have deformed into wings 34, revealing cavity 36 in tube 20.

In an alternate embodiment, sheath 28 may be eliminated. In this case, a short sheath (not shown) that is normally placed in the artery or the vein is sufficient to collapse the wings until the catheter is introduced into the artery or the vein. After the catheter enters the artery or vein it will expand to the extent required.

Figure 5:
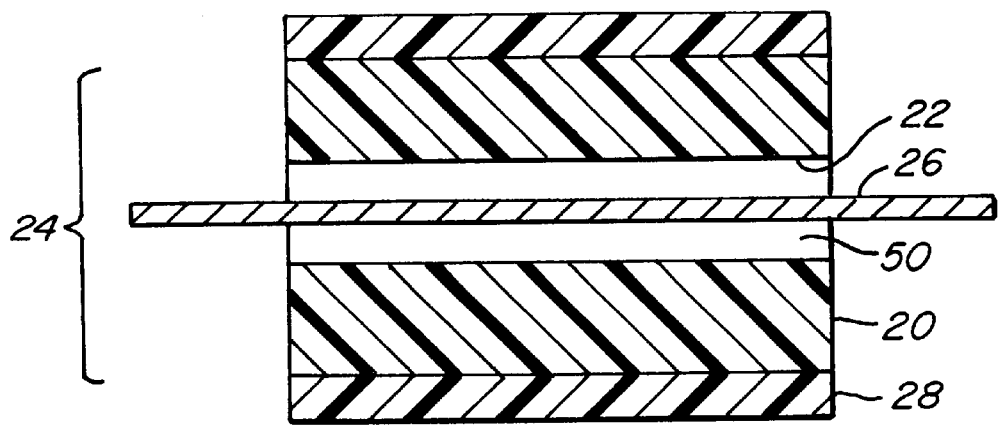
FIG. 5 is a longitudinal cross-sectional view of the preferred catheter with the intermediate portions in AY the initial, non-extended position.
Figure 5A:
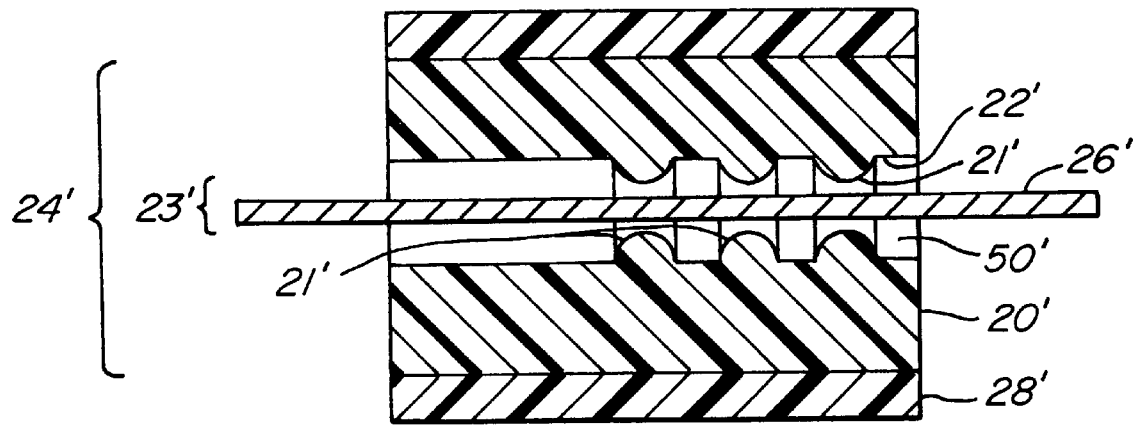
Figure 6:
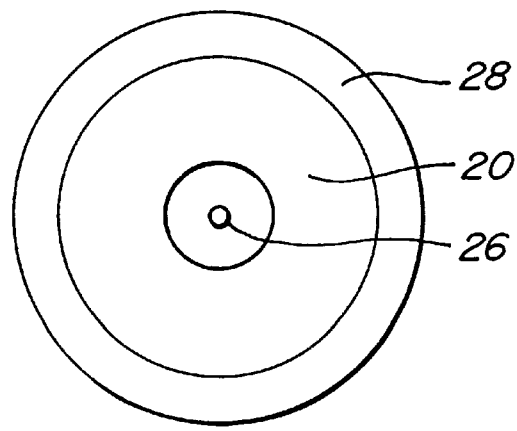
FIG. 6 is a right end elevational view of the preferred catheter with the intermediate portions in the non-extended position.

In a further embodiment shown in FIG. 5-A, a plurality of internal annular ribs 21' are formed within the inner bore 22' adjacent to the distal end. Parenthetically, structure having a counterpart in the preferred embodiment of FIG. 5 is indicated by a prime ('). The internal ribs 21' may be conveniently evenly spaced along the inner bore 22' and of an internal diameter 23' which is slightly less than the external diameter of guidewire 26'. The ribs 21' function as flow restrictors to resist axial flow of contrast media. At the same time they facilitate radial flow of the media trough the open slits (not shown).

In an example of operation, catheter 10, including tube 20 surrounded by sheath 28, is percutaneously introduced into a patient and directed through a blood vessel (not shown) and into the aorta 98, as best seen in FIG. 1. The distal end 16 is then positioned within, for example, the left ventricle 12. Upon sliding sheath 28 toward the proximal end 18 and away from the distal end, tube 20 will assume the extended position shown in FIGS. 4, 7 and 8. Contrast material forced into catheter 10 through proximal end 18 is thereby allowed to pass through cavity 36 without obstruction, forming a bolus of material within the desired endocardial chamber. FIG. 7 clearly illustrates the flow of contrast material out of cavity 36.

Figure 9:
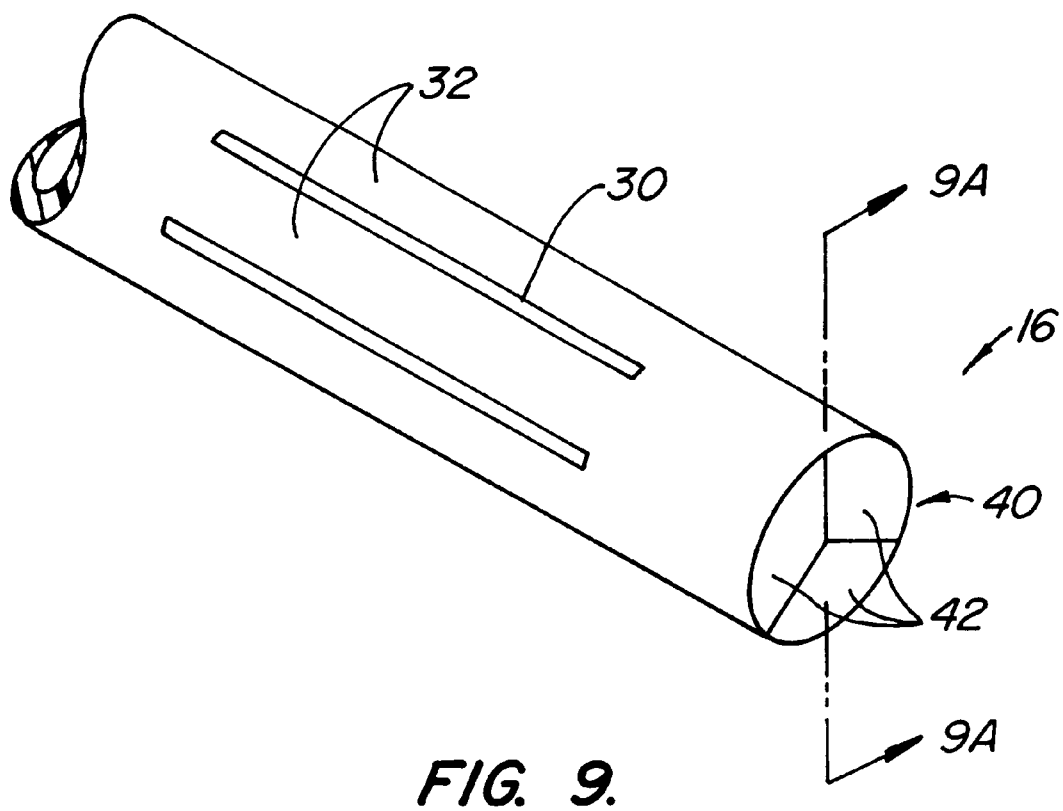
FIG. 9 is a fragmentary perspective view of the preferred catheter with valve at the distal end.
Figure 9A:
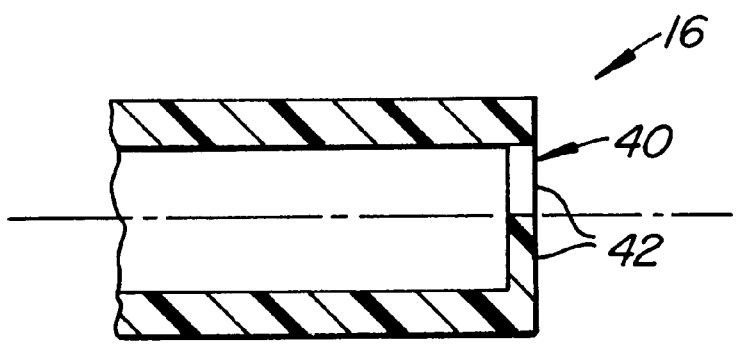
Figure 10A:
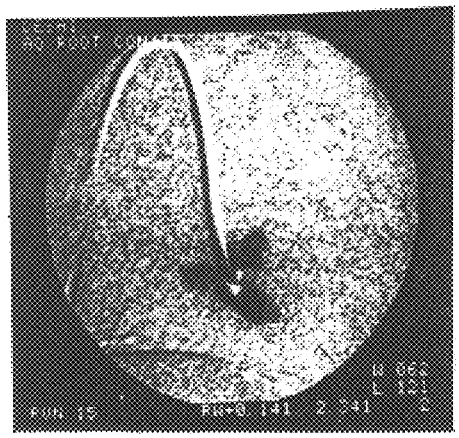
FIGS. 10-A through 10-D provide a sequence of photographs of a preferred embodiment of the catheter during an angiogram procedure.
Figure 10B:
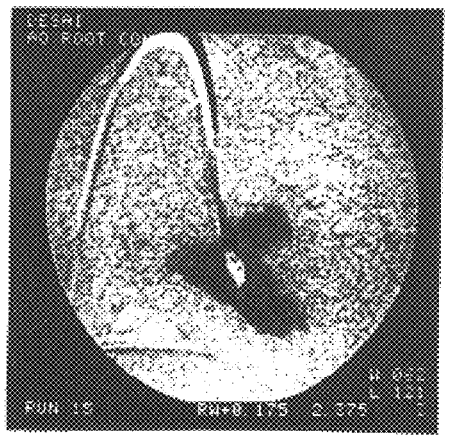
Figure 10C:
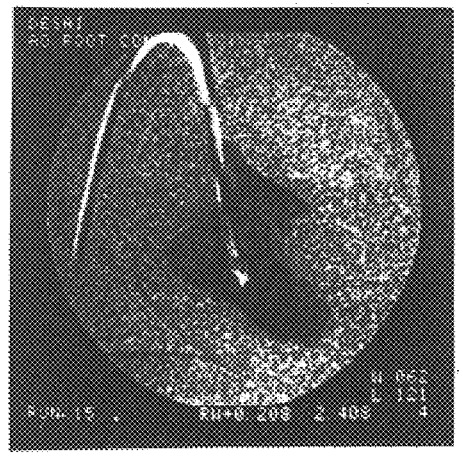
Figure 10D:
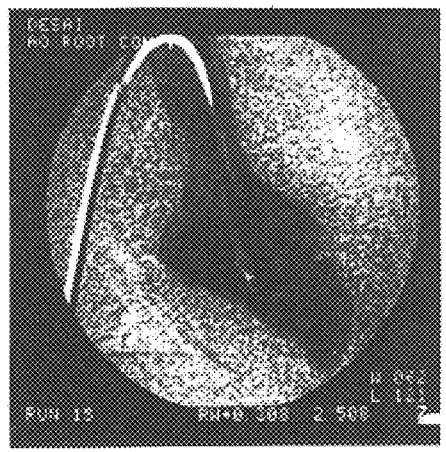

Also available for incorporation into catheter 10 is valve 40, shown in FIGS. 9 and 9-A. Valve 40 is preferably comprised of material similar to that used for tube 20, but may be made of any material having sufficient elasticity to perform the valve function in the manner described herein. When the catheter 10 is inserted into a blood vessel using a guidewire 26, as soon as the end of the guidewire engages the flaps 42 of valve 40, the flaps 42 are resilient will flex when acted on by the force of fluid pressure within passageway 22 to permit passage of the guidewire 26 until such time as it is withdrawn. When the guidewire 26 is withdrawn, valve 40 will close and remain closed, as seen in FIGS. 9 and 9-A, thus allowing for all of the fluid flowing through tube 20 to be discharged through cavity 36. While three equal flaps are shown in FIG. 9, it is to be understood that greater or lesser numbers of flaps could be utilized. For example, a single slit at the distal end 16 producing two flaps would also suffice. Inclusion of valve 40 will reduce the quantity of contrast material required for effective angiography and will eliminate end-hole jets and their concomitant effects.

A number of examples follow in order to illustrate the comparative advantages of the inventive "new" or Desai catheter described above.

EXAMPLE 1

LEFT VENTRICULAR ANGIOGRAM WITH A NEW CATHETER

FIGS. 10-A, 10-B, 10-C, 10-D, 11 and 12 provide a sequential, pictorial illustration of the operation of the current invention and a quantitative comparison to a prior art catheter. No end-hole valve is included in the embodiment shown in FIGS. 10-A through 10-D or in any of the following examples, for that matter. This accounts for the contrast material that is shown, which has been expelled from the distal end of the catheter in these figures.

FIG. 10-A shows a fluoroscope of one embodiment of the present invention, an angiographic catheter, passed through the aorta and positioned within the left ventricle of a canine heart. The catheter comprises flexible intermediate portions which have extended to become wings upon release of the surrounding sheath. The contrast material has begun to flow from cavity and the end-hole, forming a radiopaque bolus around distal end. FIGS. 10-B and 10-C show the bolus progressively increasing with the continued flow of the contrast material. FIG. 10-D shows the contrast material dispersed throughout the volume of the left ventricle, providing a complete outline of the ventricle's interior. Note the even distribution of material throughout the ventricle and the clarity of the outline provided by the preferred catheter embodiment.

Figure 11:
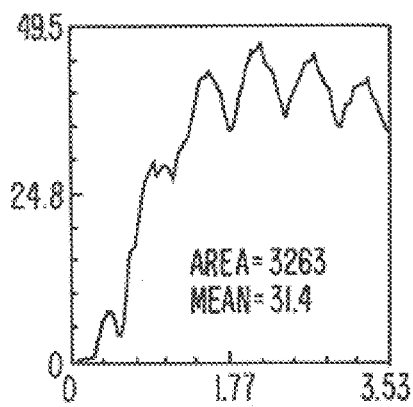
FIG. 11 is a graph of data related to contrast material volume placed within a blood vessel during an angiogram procedure using a preferred embodiment of the catheter.
Figure 12:
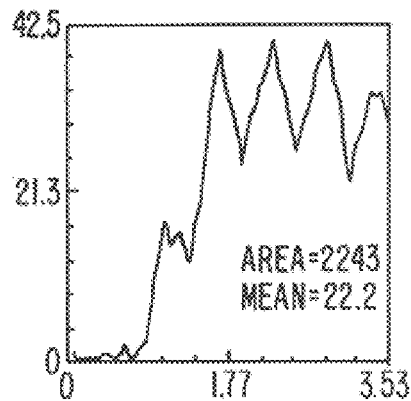
FIG. 12 is a graph of data related to contrast material volume placed within a blood vessel during an angiogram procedure using a prior art catheter.

FIGS. 11 and 12 provide an effective performance comparison of one embodiment of the inventive catheter to a prior art pigtail catheter. The catheters used for the angiograms from which the graphed data was taken have the same diameter, specifically No. 8 French. Fifteen cc of contrast material was injected using a power injector at eight cc per second. Both catheters were placed at the apex of a canine left ventricle, the. preferred placement for optimal contrast material dispersion. FIG. 11 is a graph representing the effective coverage of the ventricle over time by the subject embodiment of the present invention. FIG. 12 illustrates the same information as created by the prior art pigtail catheter. The total areas covered below the graphed lines provide a value for meaningful comparison of the two devices under nearly identical conditions. The superior ventricular coverage by the present invention when compared to the prior art catheter is clearly apparent.

EXAMPLE 2

LEFT VENTRICULAR ANGIOGRAM WITH A PIGTAIL CATHETER

The four serial pictures of left ventricular angiogram, FIGS. 15-A through 15-D, shows 15 ml of Renograffin contrast dye injected with a pigtail catheter at 8 ml per sec.

FIG. 15-A shows dye being injected in the left ventricle through a pigtail catheter. A powerful jet of dye from the end hole is seen striking the inferior (diaphragmatic) segment of left ventricular wall. This jet effect can cause premature ventricular contractions (PVC) or ventricular tachycardia (VT) rendering the angiogram unusable for calculating left ventricular volume and ejection fraction. The major bulk of dye is not injected into the left ventricular apex but superior (anterolateral) and inferior (diaphragmatic) to pigtail catheter. The dye does not opacify the left ventricular chamber from apex to aortic root in an inferior to superior direction. In this first picture, the dye is already seen to be moving towards the aortic root.

The FIG. 15-B picture shows that the end hole jet continues to strike the diaphragmatic wall. The dye has now opacified the apex. The dye is moving superior to the pigtail towards the anterobasal area and aortic root. The incoming blood from the left atrium through the mitral valve (posterobasal segment) has caused some mixing of the dye thus showing the faint outline of the posterobasal and anterolateral segments of the heart.

The FIG. 15-C picture shows a very small amount of dye being injected into the left ventricular wall from end hole and side hole jets on the pigtail. These are the triangular shaped darker shadows seen all around the pigtail loop. The dye is mostly concentrated in the apex, inferior cavity and area superior to the pigtail. The posterobasal segment near the mitral valve and left ventricular outflow area has a very small amount of dye, barely opacifing the outline of that area. Also aortic root is faintly visualized as some dye has been ejected out of the left ventricle without fully opacifing the left ventricle.

This FIG. 15-D picture shows almost all the dye is injected into the left ventricle. The entire left ventricle is still not well opacified. The dye in the posterobasal segment near the mitral valve and left ventricular outflow tract does not well opacify these areas. A significant amount of dye is ejected out into the aortic root which is more densely outlined compared to the previous picture. As the entire left ventricular chamber is not well opacified, this is not an ideal angiogram to determine left ventricular volume and ejection fraction. It took 660 msec (20 frames) to opacify the left ventricle.

EXAMPLE 3

LEFT VENTRICULAR ANGIOGRAM WITH TIME DENSITY CURVES SHOWING COMPARISON OF NEW CATHETER VERSUS PIGTAIL CATHETER NEAR THE APEX

Figure 13A:
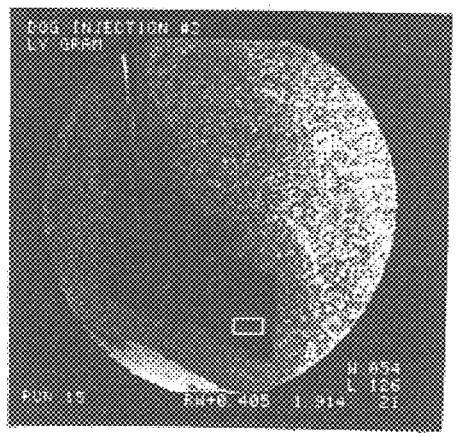
FIG. 13-A is a photo of a left ventricular angiogram with the new catheter.
Figure 13B:
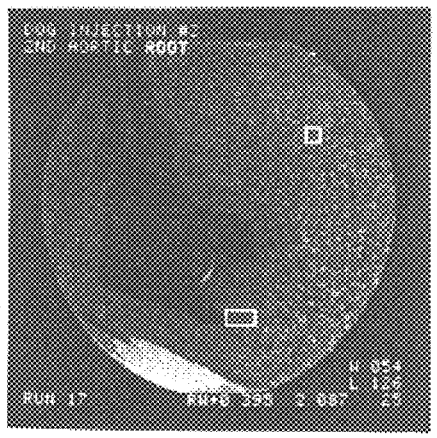

FIG. 13-A shows left ventricular angiogram (15 ml injection at 8 ml per second) with new catheter. Renograffin Contrast Dye (dye) almost opacifies the left ventricle with very small amount ejected from left ventricle to aortic root, which is barely opacified. The bulk of dye from this catheter is injected into the Apex.

The graph of FIG. 11 shows time density curves generated from the area marked by a window at the Apex in FIG. 13-A. This window is compared with a window outside the left ventricle. The X axis shows elapsed time and Y axis shows density of dye. The fluctuation in the curve is due to mixing and dilution of dye from incoming blood, dye being injected from the catheter tip, contraction of the Apex and ejection of dye from the ventricle. The curve is smooth with rapid and. persistent opacification of the area of interest (Apex). The curve starts to plateau at 1.34 secs.

The picture of FIG. 13-B shows left ventricular angiogram (15 ml injected at 8 ml per sec) with pigtail catheter. Renograffin Contrast Dye (dye) is injected away from the Apex. Large area of Apex and cavity superior to Apex is unopacificed. Also a significant amount of the dye is ejected from left ventricle to aortic root opacificing the aortic root with almost the same density.

The graph of FIG. 12 shows time density curves generated from the area marked by a window at the apex in FIG. 13-B. This window is compared with a window outside the left ventricle. The X axis shows elapsed time and Y axis shows density of dye. The fluctuation in the curve is due to mixing and dilution of dye from incoming blood, dye being injected from the catheter tip, contraction of the Apex and ejection of dye from the ventricle. The fluctuations in this curve are more pronounced compared to the curve in FIG. 11 (new catheter) because of the increased amount of dye being ejected out from left ventricle to aortic root and turbulence caused by mitral valve motion with each beat. The area under the curve is 31% less compared to the new catheter. The curve starts to plateau at 1.51 sec.

EXAMPLE 4

AORTIC ROOT ANGIOGRAM AND NONSELECTIVE CORONARY ANGIOGRAPHY

Figure 14A:
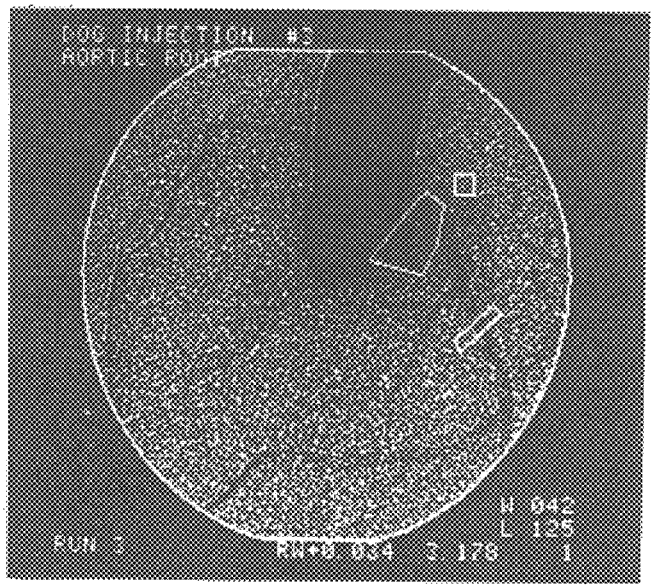
FIG. 14-A is a photo showing a densely opacified aortic root and right and left coronary arteries with its branches.
Figure 14B:
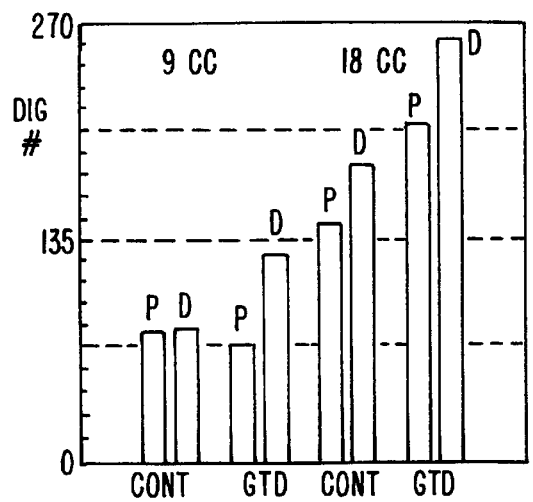
Figure 14C:
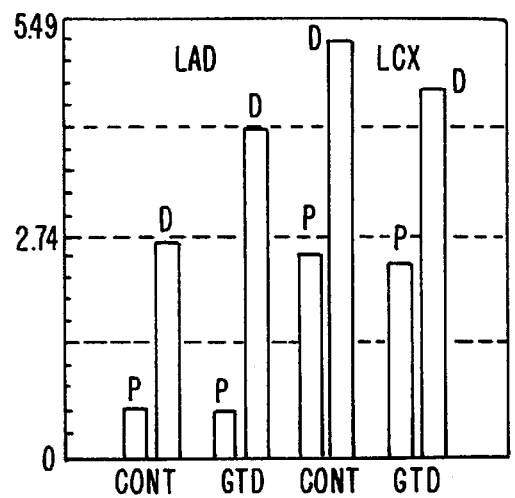

The picture of FIG. 14-A shows an aortic root angiogram with pigtail or new catheter showing densely opacified aortic root, right and left coronary arteries with its branches. For both catheters two injections are performed in the aortic root at 9 ml and 18 ml (8 ml per sec). A window is placed on the left aortic cusp to compare the maximum density with the smaller background window which is just above the cusp. The second window is placed on the left coronary artery to compute the maximum density with reference to the same background window.

The graph of FIG. 14-B picture shows comparison of maximum density of dye in the cusp at 9 ml and 18 ml. At 9 ml there is no significant difference between the new catheter ("D") and pigtail catheter ("P"). At 18 ml the new catheter shows about 15% more density of dye.

The FIG. 14-C picture shows maximum opacification of coronary arteries. The picture shows nonselective coronary angiogram of left anterior descending and left circumflex coronary arteries. The injection was in the aortic root with Renograffin 15 ml at 8 ml per sec. The bargraph shows the maximum density of dye in the coronary artery with pigtail or new catheter. In both, anterior descending and left circumflex arteries the new catheter opacification is 100% more dense than the pigtail catheter.

EXAMPLE 5

PATTERNS OF RENOGRAFFIN CONTRAST DYE DISTRIBUTION IN THE LEFT VENTRICLE DURING LEFT VENTRICULAR ANGIOGRAM WITH PIGTAIL CATHETER

Figure 16A:
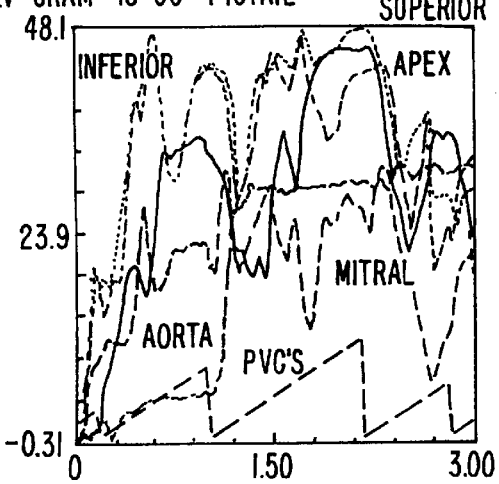
FIG. 16-A is a graph of various dye density versus time curves for a pigtail catheter.
Figure 16B:
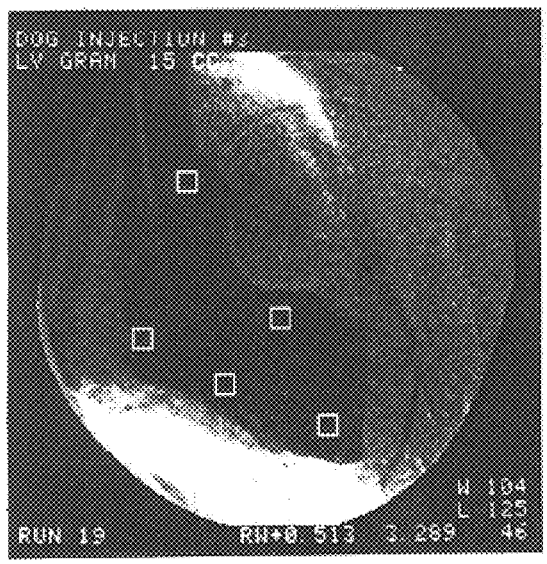

FIGS. 16-A and 16-B show patterns of distribution of contrast matrial in the left ventricle. To uniformly opacify left ventricle, ideal site of contrast injection is in the apex. When dye is injected in the apex, opacification of left ventricle occurs in inferior to superior direction (from apex to aortic root). The injection of dye in the apex minimizes the ejection of dye from aortic root and achieves opacification of the chamber with minimal loss.

In the FIG. 16-B picture, dye is injected into the left ventricle through a pigtail catheter (15 ml at 8 ml per sec). The small squares show areas of interest to compute the density time curve of dye in that region. The areas are as follows:

APEX (apical)
SUPERIOR (anterolateral)
INFERIOR (diaphragmatic)
MITRAL VALVE (posterobasal)
AORTIC ROOT Referring to FIG. 16-A, the various curves are density of dye versus time curves. The lowest curve is the R wave curve showing 3 heart beats including a PVC and a post PVC beat. All curves are together for a very short time. The apex curve lags behind suggesting that dye is not continuously injected in the apex. The inferior and superior curves show identical density time relationship with wild fluctuations suggesting ejection of dye and dilution of dye from incoming blood. The apex density increases at 2.4 sec suggesting that the dye is concentrating in the apex late. At 1.05 sec there is a major ejection of dye from the left ventricle into the aorta. This forceful prolonged ventricular contraction is produced by a post premature ventricular beat.

This pigtail catheter does not uniformly inject the dye in the apex and thus does not uniformly opacify the ventricle from apex to aortic root in the inferior to superior direction. This results in nonuniform opacification of the left ventricle with loss of dye by ejection into the aortic root. Also because of jet effects, premature ventricular contractions and ventricular tachycardia can make left ventricular angiogram nonusable for calculation of left ventricular volume and ejection fraction.

EXAMPLE 6

PATTERNS OF RENOGRAFFIN CONTRAST DYE DISTRIBUTION IN THE LEFT VENTRICLE DURING LEFT VENTRICULAR ANGIOGRAM WITH NEW CATHETER

Figure 17A:
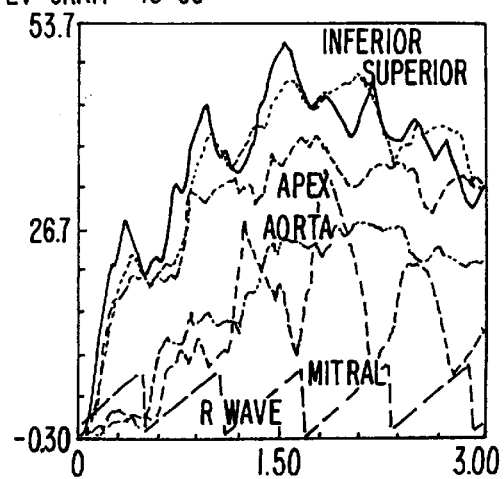
FIG. 17-A is a graph similar to FIG. 16-A above graphing various density and time curves for a new catheter; and, FIG. 17-B is a photo similar to FIG. 16-B above showing dye being injected into the left ventricle through a new catheter.
Figure 15A:
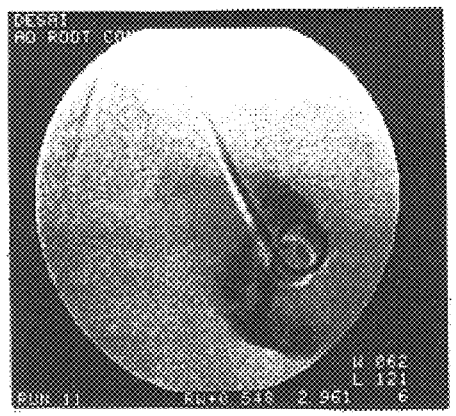
FIGS. 15-A through 15-D provide a prior art sequence of photographs of a pigtail catheter during an angiogram procedure.
Figure 15B:
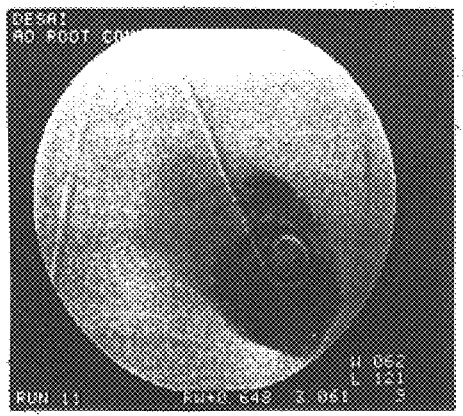
Figure 15C:
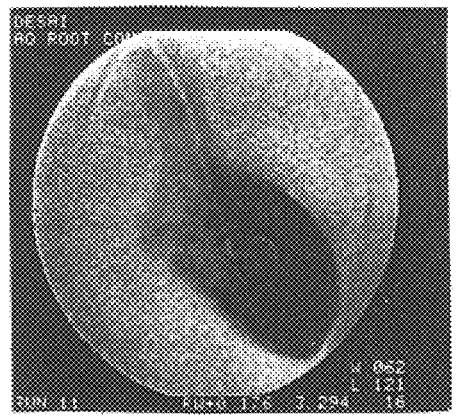
Figure 15D:
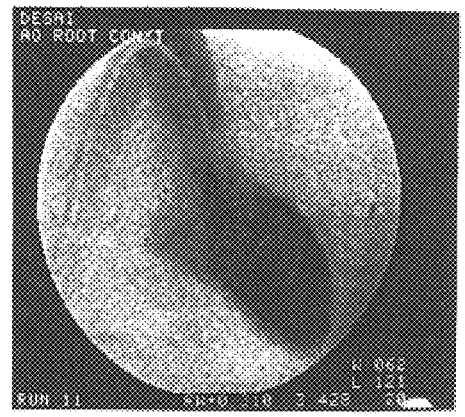
Figure 17B:
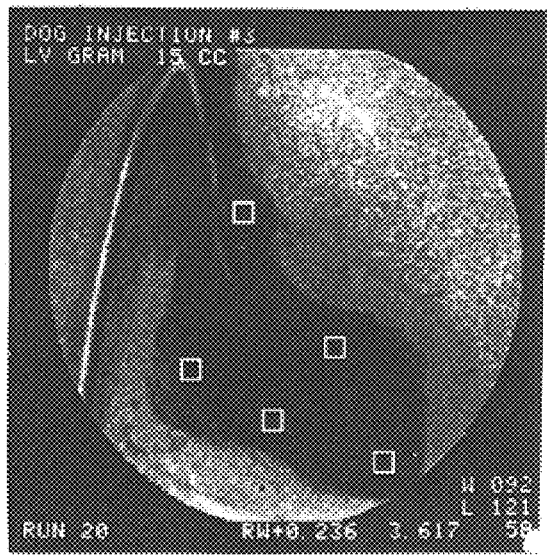

These two figures, FIGS. 17-A and 17-B, show patterns of distribution of contrast matrial in the left ventricle. to uniformly opacify left ventricle, ideal site of contrast injection is the apex. When the dye is injected in the apex, opacification of left ventricle occurs in inferior to superior direction (from apex to aortic root). The injection of dye in the apex minimizes the ejection of dye from aortic root and achieves opacification of the chamber with minimal loss.

In the picture of FIG. 17-B dye is injected into the left ventricle through a pigtail catheter (15 ml at 8 ml per sec). The small squares show areas of interest to compute the density time curve of dye in that region. The areas are as follows:

APEX (apical)
SUPERIOR (anterolateral)
INFERIOR (diaphragmatic)
MITRAL VALVE (posterobasal)
AORTIC ROOT Most of the dye is injected into the apex, inferior and superior aspect of the left ventricle. All three curves remain together without wild fluctuation suggesting the majority of dye being injected in these areas. The ejection from ventricle into aortic root is also more uniform and occurs after 1.125 sec. This angiogram suggests opacification of the left ventricle occurs from inferior to superior direction (from apex to aortic root).

The mitral valve curve fluctuations are due to incoming blood from the left atrium diluting and mixing the dye.

The new catheter uniformly opacifies the left ventricle from apex to aortic root without significantly losing the dye before opacification is completed.

Various details of the implementation and method are merely illustrative of the invention. It will be understood that various changes of details may be within the scope of the invention, which is to be limited only by the appended claims.

What is claimed is:

1. A catheter comprising:

an elongated tubular member having a proximal end and a distal end;

said tubular member including a passageway extending throughout the length of the tube and forming a wall proximal and distal openings;

a plurality of circumferentially-spaced longitudinally extending slits through said wall adjacent the distal end defining a plurality of circumferentially-spaced longitudinally extending flexible intermediate portions of said wall, said flexible intermediate portions capable of forming a plurality of wings extending from said tube to provide for the discharge of fluid from the passageway out through said wall through the open slits defined between said wings, wherein said passageway has space so that fluid is provided to the distal end from the proximal end by way of said passageway; and a valve at the distal end of the tubular member;

wherein said catheter is insertable over a guidewire within said passageway; and said valve normally sealingly closes said distal opening, said valve sealing around said guidewire during the passage of said guidewire through said tube and valve.

2. The catheter of claim 1 wherein the valve is adapted to at least partially close said passageway at the distal end of said tube, said valve means comprising a plurality of resilient flaps which flex when acted on by the force of fluid pressure originating within said passageway.

3. The catheter of claim 1 wherein said flexible intermediate portions are normally positioned to form said wings.

4. The catheter of claim 1 further including an external, removable cannula dimensioned to fit over and collapse said tube to its maximum length and minimum width and to compress said wings until they return to a retracted position with said slits in a closed position.

5. The catheter of claim 1 including means for expanding said intermediate portions away from said tube to provide lateral openings for the discharge of fluid from the passageway.

6. The catheter of claim 1 further including at least one restrictor within said passageway for resisting axial flow thereby.

7. The catheter of claim 6 wherein said at least one restrictor comprises at least one protuberance on said wall within said passageway.

8. The catheter of claim 7 wherein said at least one restrictor comprises a plurality of spaced, annular ribs.

9. A catheter comprising:

an elongated tubular member having a proximal end and a distal end;

said tubular member having a thin wall defining a passageway extending throughout the length of the tube and forming proximal and distal openings;

a plurality of circumferentially-spaced longitudinally extending slits through said thin wall adjacent the distal end defining a plurality of circumferentially-spaced longitudinally extending flexible intermediate portions of said thin wall, adjacent said slits;

said flexible intermediate portions normally forming a plurality of wings extending from said tube with open slits therebetween to provide for the discharge of fluid from the passageway through said open slits in said thin wall near said distal end, wherein said passageway has space so that fluid is provided to the distal end from the proximal end by way of said passageway;

an external, removable cannula dimensioned to fit over and collapse said tube to its maximum length and minimum width and to compress said wings until they return to a position with said slits in a closed position; and a valve normally sealingly closing said distal end of said passageway, said valve adapted to seal against passage of fluid from said passageway through said distal opening during passage of said guidewire through said tube and valve.

10. A catheter comprising:

an elongated tubular member having a proximal end and a distal end;

said tubular member having a thin wall defining a passageway extending throughout the length of the tube and forming proximal and distal openings;

a plurality of circumferentially-spaced longitudinally extending slits through said thin wall adjacent the distal end defining a plurality of circumferentially-spaced longitudinally extending flexible intermediate portions of said thin wall, adjacent said slits;

said flexible intermediate portions normally forming a plurality of wines extending from said tube with open slits therebetween to provide for the discharge of fluid from the passageway through said open slits in said thin wall near said distal end, wherein said passageway has space so that fluid is provided to the distal end from the proximal end by way of said passageway;

an external, removable cannula dimensioned to fit over and collapse said tube to its maximum length and minimum width and to compress said wings until they return to a position with said slits in a closed position; and a valve means for at least partially closing said distal opening, said valve means comprised of a plurality of resilient flaps which will flex when exposed to the force of fluid pressure originating within said passageway.

11. A catheter comprising:

an elongated tubular member having a proximal end and a distal end;

said tubular member having a thin wall defining a passageway extending throughout the length of the tube and forming proximal and distal openings;

a plurality of circumferentially-spaced longitudinally extending slits through said thin wall adjacent the distal end defining a plurality of circumferentially-spaced longitudinally extending flexible intermediate portions of said thin wall, adjacent said slits;

said flexible intermediate portions normally forming a plurality of wings extending from said tube with open slits therebetween to provide for the discharge of fluid from the passageway through said open slits in said thin wall near said distal end, wherein said passageway has space so that fluid is provided to the distal end from the proximal end by way of said passageway;

an external, removable cannula dimensioned to fit over and collapse said tube to its maximum length and minimum width and to compress said wings until they return to a position with said slits in a closed position; and at least one non-metallic restrictor within said passageway for resisting axial flow thereby.

12. The catheter of claim 11 wherein said at least one restrictor comprises at least one protuberance on said wall within said passageway.

13. The catheter of claim 12 wherein said at least one restrictor comprises a plurality of spaced, annular ribs.

14. A catheter comprising:

an elongated tubular member having a proximal end and a distal end;

said tubular member including a passageway extending throughout the length of the tube and forming a wall proximal and distal openings;

a plurality of circumferentially-spaced longitudinally extending slits through said wall adjacent the distal end defining a plurality of circumferentially-spaced longitudinally extending flexible intermediate portions of said wall, said flexible intermediate portions capable of forming a plurality of wings extending from said tube to provide for the discharge of fluid from the passageway out through said wall through the open slits defined between said wings, wherein said fluid is provided to the passageway from the proximal opening; and at least one non-metallic restrictor within said passageway for resisting axial flow through the passageway, the at least one restrictor located near the distal opening of the tubular member.

15. The catheter of claim 14, wherein said at least one restrictor comprises at least one protuberance on said wall within said passageway.

16. The catheter of claim 15 wherein said restrictors comprise a plurality of spaced, annular ribs.

* * * * *